United States Patent
Suddaby

(10) Patent No.: US 9,364,241 B2
(45) Date of Patent: Jun. 14, 2016

(54) DISK PREPARATION TOOL WITH FLEXIBLE CUTTING ELEMENT

(76) Inventor: Loubert Suddaby, Orchard Park, NY (US)

( * ) Notice: Subject to any disclaimer, the term of this patent is extended or adjusted under 35 U.S.C. 154(b) by 1012 days.

(21) Appl. No.: 13/073,925

(22) Filed: Mar. 28, 2011

(65) Prior Publication Data

US 2012/0071880 A1    Mar. 22, 2012

Related U.S. Application Data

(63) Continuation of application No. 11/692,878, filed on Mar. 28, 2007, now Pat. No. 7,914,534.

(60) Provisional application No. 60/786,394, filed on Mar. 28, 2006.

(51) Int. Cl.
*A61B 17/16*    (2006.01)

(52) U.S. Cl.
CPC ......... *A61B 17/1659* (2013.01); *A61B 17/1671* (2013.01); *A61B 17/1666* (2013.01)

(58) Field of Classification Search
USPC ............ 606/79–81, 83–85; 433/51, 125, 142, 433/166; 407/29.11–29.13
See application file for complete search history.

(56) References Cited

U.S. PATENT DOCUMENTS

| | | | |
|---|---|---|---|
| 3,737,984 A * | 6/1973 | Pietroski | ............................ 407/1 |
| 3,852,843 A | 12/1974 | Metz | |
| 4,685,181 A * | 8/1987 | Schwartz | .................. 407/29.13 |
| 5,601,556 A | 2/1997 | Pisharodi | |
| 5,733,288 A * | 3/1998 | Allen | ............................... 606/79 |
| 6,083,228 A | 7/2000 | Michelson | |
| 6,283,971 B1 * | 9/2001 | Temeles | .......................... 606/81 |
| 6,517,544 B1 | 2/2003 | Michelson | |
| 6,537,279 B1 | 3/2003 | Michelson | |
| 6,562,045 B2 | 5/2003 | Gil et al. | |
| 6,692,501 B2 | 2/2004 | Michelson | |
| 6,740,090 B1 * | 5/2004 | Cragg et al. | .................... 606/79 |
| 6,755,865 B2 | 6/2004 | Tarabishy | |
| 6,902,568 B2 | 6/2005 | Serhan | |
| 6,966,912 B2 | 11/2005 | Michelson | |
| 7,147,642 B2 | 12/2006 | Grinberg et al. | |
| 7,294,131 B2 | 11/2007 | Kunzler | |
| 2003/0236523 A1 | 12/2003 | Johnson et al. | |
| 2004/0087957 A1 | 5/2004 | Kunzler | |
| 2004/0162563 A1 | 8/2004 | Michelson | |
| 2004/0267269 A1 * | 12/2004 | Middleton et al. | .............. 606/84 |
| 2005/0015091 A1 | 1/2005 | Bryan et al. | |
| 2005/0049601 A1 | 3/2005 | Keller | |
| 2006/0004369 A1 * | 1/2006 | Patel et al. | ....................... 606/79 |

* cited by examiner

*Primary Examiner* — Anu Ramana
(74) *Attorney, Agent, or Firm* — Davis & Bujold PLLC; Michael J. Bujold

(57) ABSTRACT

A tool for preparing vertebral surfaces following a discectomy has a body and a rotary cutting tool mounted at the distal end of a lever which extends through the body. The proximal end of the lever can be squeezed toward the body to force the cutting tool against the vertebral surface facing it, while the tool is rotated by turning a crank supported on the tool body, or by a motor. The cutting tool is preferably a flexible rasp or blade which can conform to and control the convexity of the prepared surface.

2 Claims, 4 Drawing Sheets

DISK PREPARATION TOOL WITH FLEXIBLE CUTTING ELEMENT

This application is a continuation of copending application Ser. No. 11/692,878 filed Mar. 28, 2007, which claimed benefit of provisional patent application 60/786,394, filed Mar. 28, 2006.

BACKGROUND OF THE INVENTION

This invention relates to an intervertebral disc removing device. It allows for removal of the nucleus pulpous of an intervertebral disc, as well as the resurfacing of the vertebral end plate in preparation for nucleus replacement procedures or interbody fusion techniques.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in the horizontal attitude. As a result, the stresses acting upon the human backbone (or "vertebral column") are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five in the low back or lumbar region. There are also five bones in the pelvic or sacral region which are normally fused together and form the back part of the pelvis. This column of bones is critical for protecting the delicate spinal cord and nerves, and for providing structural support for the entire body.

Between the vertebral bones themselves exist soft tissue structures-discs-composed of fibrous tissue and cartilage which are compressible and act as shock absorbers for sudden downward forces on the upright column. More importantly, the discs allow the bones to move independently of each other, as well. Unfortunately, the repetitive forces which act on these intervertebral discs during repetitive day-to-day activities of bending, lifting and twisting cause them to breakdown or degenerate over time.

Presumably because of humans' upright posture, their intervertebral discs have a high propensity to degenerate. Overt trauma, or covert trauma occurring in the course of repetitive activities, disproportionately affect the more highly mobile areas of the spine.

Disruption of a disc's internal architecture leads to bulging, herniation or protrusion of pieces of the disc nucleus and eventual disc space collapse. Resulting mechanical and even chemical irritation of surrounding neural elements (spinal cord and nerves) cause pain, attended by varying degrees of disability. In addition, loss of disc space height relaxes tension on the longitudinal spine ligaments, thereby contributing to various types of spinal instability such as spinal curvature, ligamentous laxity or instability and spondylolithesis.

The time-honored method of addressing neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

Once the disc has been removed, an implant may be installed in its place. Prior to implantation, in many situations, it is desirable or necessary to smooth or recontour the opposing vertebral surfaces. Proper preparation can be difficult and time-consuming.

U.S. Pat. No. 6,537,279 depicts a device for preparing an intervertebral endplate with an abrading element which is disc shaped.

In contrast, the abrading element of my device is linear and rotated like a propeller so it can be inserted through a much smaller opening in a disc and lends itself to minimally invasive techniques. Prior devices having disc-shaped cutters required an opening to be made in the disc annulus comparable in size to the diameter of the disc. The slender cutter of the present invention can be inserted through an opening much smaller than that required by a disc shaped cutter and hence is superior for minimally invasive techniques.

The present device also does not require screws to hold it in place in the disc space; moreover, the cutting surface can be expanded within the disc space to achieve greater force against the end plates. In contrast, the distance between the disc shaped cutters in the patent mentioned above is fixed by the gear drive mechanism used to drive both cutting discs simultaneously.

Because the abrading surfaces can be pressed apart while within the disc space, varying disc heights can be accommodated with a single device.

The device of the present invention has a flexible cutting blade which conforms itself to various contours in the endplate whereas prior cutting surfaces are fixed and their contours are predetermined, not variable. The propeller-like shape of the cutting or abrading surface is superior because it can be inserted through an opening the width of the propeller blade and still resurface a disc sized the length of the propeller blade.

One embodiment of the present invention has a dual shaft design which allows the abrading surfaces to be expanded away from each other to allow for use in discs of any height without any change of the drive means or the abrading elements. Additionally, the dual shaft design is superior as it allows the working cutting blades to be driven apart from each other to increase the force upon the blades while the blades are still in motion.

SUMMARY OF THE INVENTION

An object of the invention is to improve the speed and quality of vertebral surface preparation following a discectomy.

Another object is to provide a tool that can be inserted into an annulotomy in an intervertebral disc to simultaneously or sequentially perform the functions of disc removal, end plate preparation, irrigation and suctioning without having to be removed.

A further object is to provide a tool for disc removal and end plate resurfacing which can be inserted into a disc space, centered (by means of x-ray localization) and fixated in position by a pin located at the rotary head, the pin serving to engage a vertebral surface and steady the tool.

These and other objects of the invention are attained by the surgical tool described and claimed below.

BRIEF DESCRIPTION OF THE DRAWINGS

In the accompanying drawings.

DESCRIPTION OF A PREFERRED EMBODIMENT OF THE INVENTION

Figure 1:
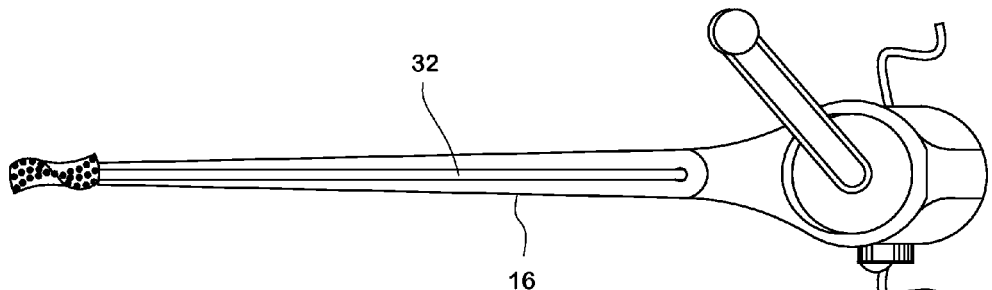
FIG. 1 is a top plan view of a tool embodying the invention.
Figure 2:
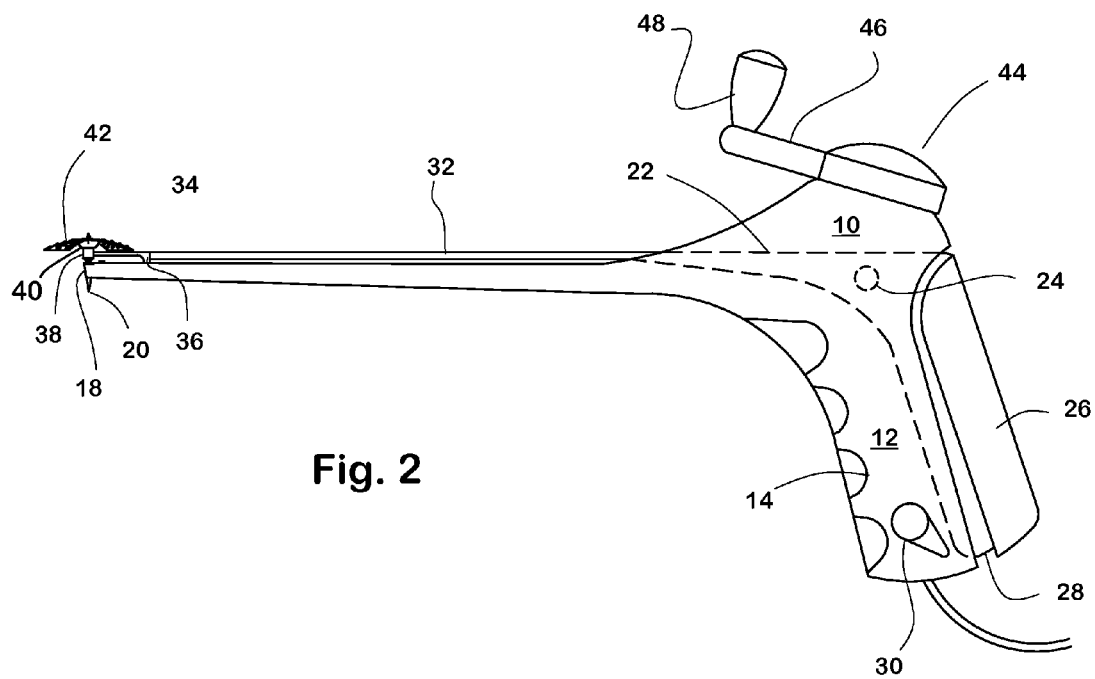
FIG. 2 is a left side view thereof.
Figure 3:
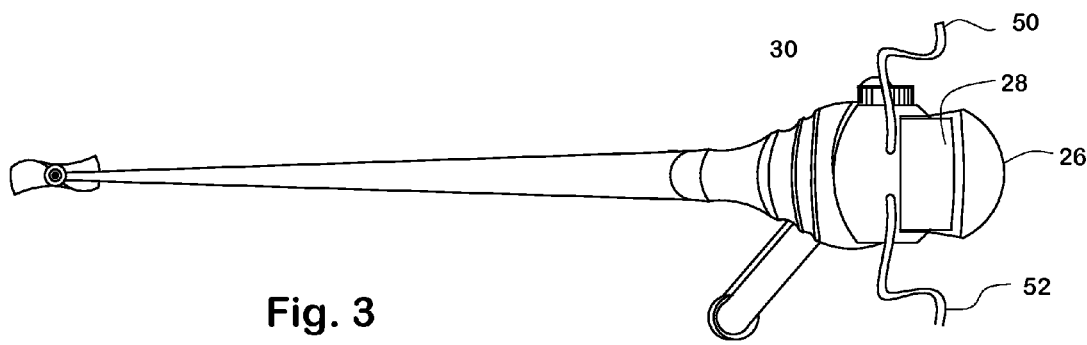
FIG. 3 is a bottom plan view thereof.

A tool embodying the invention has a pistol-shaped body 10 whose lower portion is shaped to form a hollow grip 12 preferably having finger depressions 14 as shown in FIG. 1. The forward or distal end of the body is an elongate probe 16 that tapers towards its tip 18. A fixed centering pin 20 extends downward from the tip.

The body contains a portion of a lever 22, which is supported on a transverse pivot pin 24 seated in holes (not shown) in the body. Alternatively, the pin might be molded integrally with the body and holes formed in the lever, or pin ends could be molded on the lever, for seating in the holes in the body.

The proximal end of the lever 22 extends downwardly, to the rear of the pivot pin. Its rear surface 26 is rounded to fit against the palm of a surgeon. A reduced-thickness guide portion 28 formed to the front of the rear surface is sized to slide in and out of the cavity in the grip, to maintain alignment between the parts.

A lock actuating lever 30 at the bottom of the grip can be moved between a safe position preventing movement of the lever and an operating position permitting movement.

The distal end 32 of the lever is a slender tube substantially parallel to the probe 16, and having a distal terminus 34 near the tip 18. Alignment between the probe and the tube is maintained by an alignment stem 36 which extends from the shaft into a hole or slot in the probe. A right angle drive mechanism 38 is fixed at the terminus 34. The mechanism has an output shaft (not shown) that rotates about a head axis "A". A rotary head 40 is secured to the output shaft, and a flexible rasp 42 or blade is mounted on the rotary head. The blade or rasp is designed to cut material from an intervertebral disc end plate and to direct cuttings downward to a suction port for removal. It can be raised or lowered mechanically by the lever mechanism to enhance its efficiency and effectiveness. Its flexibility enables it to conform to irregularities in the shape of intervertebral disc or the adjacent end plate, so that it does not have to grind a geometric surface of revolution on the end plate.

Preferably, the shape of the blade is propeller-like, and its length is substantially greater than its width. The aspect ratio (length-to-width) of the blade is preferably at least 3:1, and may be substantially greater than that. The narrower the blade is, the smaller a surgical aperture it may be inserted through.

The thickness and material of the blade are chosen so that the blade, without being flaccid, can deflect from its original shape to follow irregularities it encounters in the end plate without undergoing any permanent deformation so that it always returns to its original shape when load is released. It should be sufficiently stiff (resistant to bending) that its outer edges remain in contact with the end plate in use, yet not so stiff that it cuts more at the tips of the blade than at the center, or so stiff that it is difficult for the surgeon to apply enough squeezing force to the handle to establish full contact between the blade and the endplate. Ideally, the blade should apply evenly distributed pressure to the end plate. An assortment of blades of different sizes, shapes, stiffnesses and surface may be provided for the surgeon to choose from.

The rasp head is turned, an will be explained, by a crank mechanism shown generally as 44, at the proximal end of the tool. The mechanism comprises a crank arm 46 having a handle 48, and a crank shaft, not shown, inside the tool. A transmission device, such as a beveled gear set or a flexible drive cable, connects the crank shaft to a drive shaft (not shown) inside the tube. The drive shaft serves as, or is connected to, the input shaft of the right angle drive so that, when the crank is turned, the rotary head and the rasp mounted thereon turn as well.

A water supply line 50 and a suction line 52 extend along parallel paths through the body of the tool, terminating at neighboring outlet ports 54, 56 directed at the bottom of the rasp.

Figure 4:
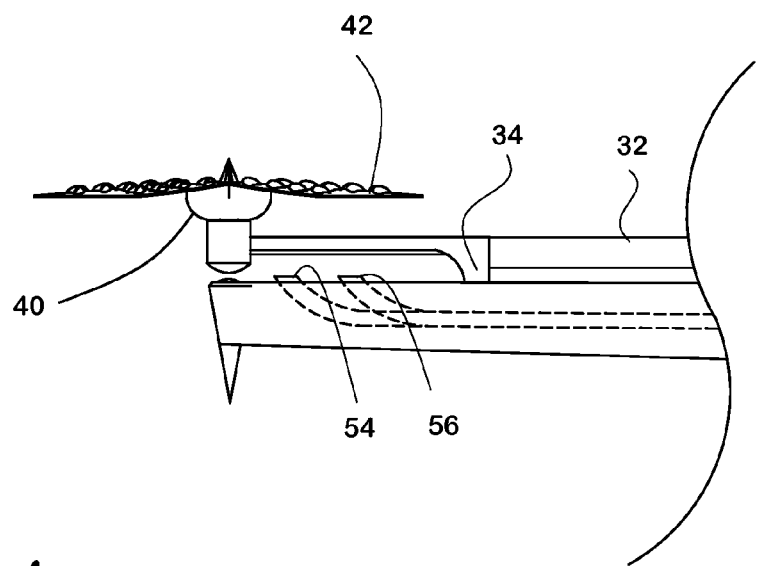
FIG. 4 is an enlargement of a portion of FIG. 2, showing the cutting head of the tool.
Figure 5:
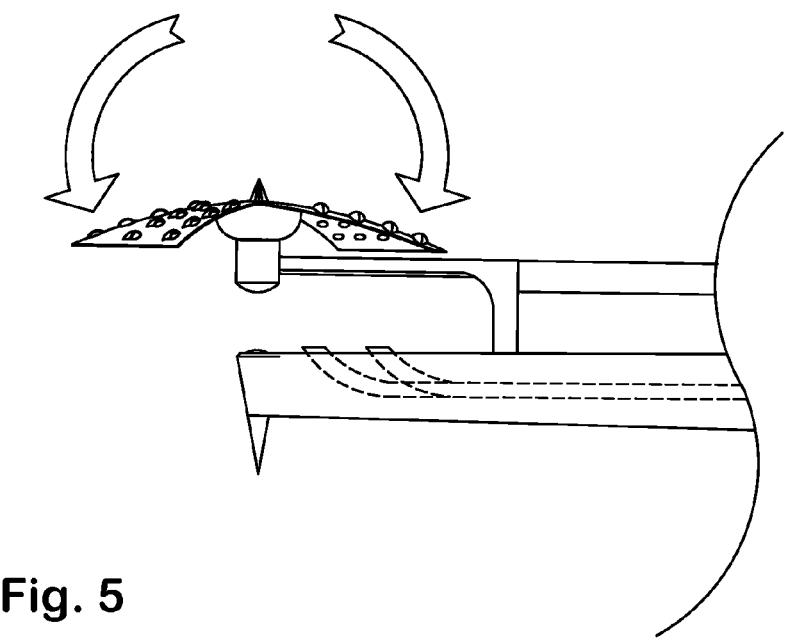
FIG. 5 is a similar view, showing flexure of a rasp mounted on the head.
Figure 6:
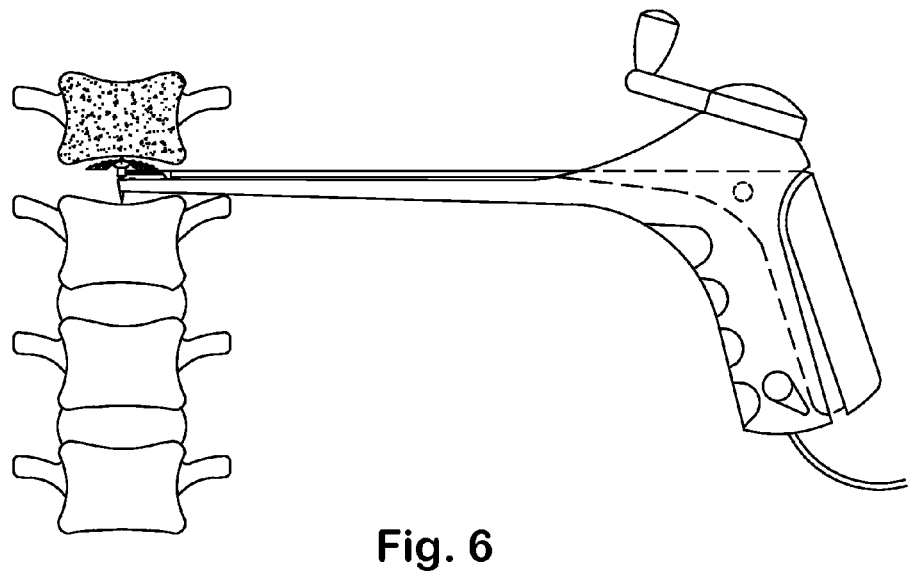
FIG. 6 illustrates placement of the tool head within a surgical site.
Figure 7:
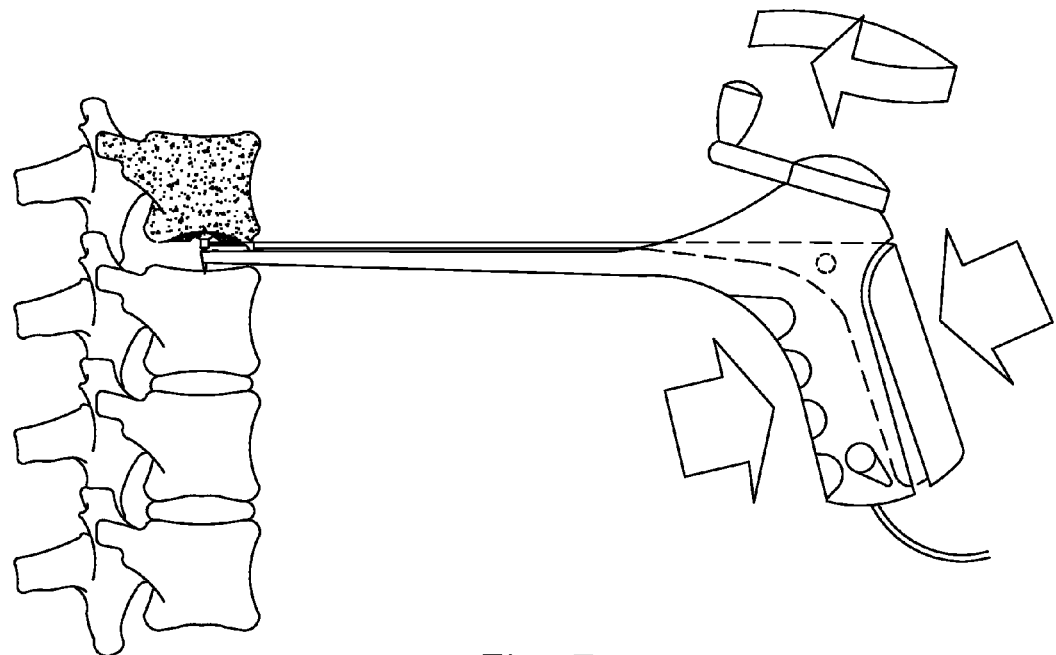
FIG. 7 shows the tool being used to prepare a vertebral surface.

In use, a surgeon, having made a suitable incision and having performed a discectomy, inserts the tip of the tool through the incision into the space previously occupied by the disc. The surgeon carefully centers the tip of the tool in the intervertebral cavity, as shown in FIG. 6, and presses the centering pin into the surface of the vertebra opposite that being prepared to steady the tip as the tool is operated. Now the rasp may be caused to bear against the subject surface by applying controlled pressure to the palm actuator (FIG. 7). Because the rasp is flexible, the more pressure is applied (compare FIGS. 4 and 5), the more the rasp will bend as it engages the convex surface. By controlling the pressure, the degree of convexity in the subject surface can be controlled as well.

The rasp is rotated by turning the crank handle, and as it rotates, the rasp removes material from the subject surface. The cuttings, flushed away from the rasp by incoming water from the supply line, are removed from the site by the suction line.

This invention is subject to modification and improvement, and numerous changes may occur to a person of ordinary skill in this field. Details of the drive train between the crank shaft and the right angle drive are matters of ordinary skill.

Figure 8:
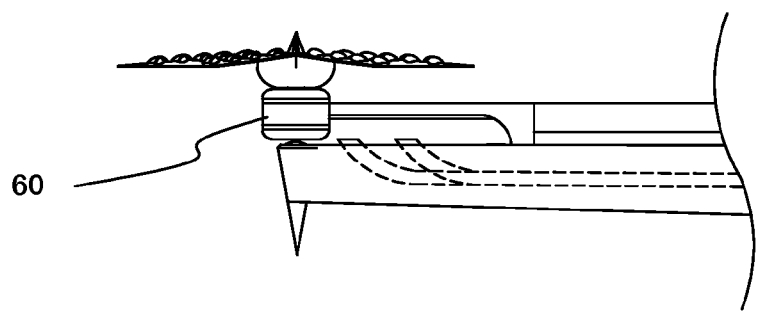
FIG. 8 shows a tool in which the cutting head is driven by a small motor.

Alternatively, the crank may be replaced by a motor, such as a hydraulic motor driven by the supply water; that motor could be placed in the body of the tool, or possibly in the position of the right angle drive, as shown in FIG. 8—where the motor is designated by reference numeral 60—in which case no drive train would be needed. The motor might be electric, hydraulic or pneumatic. Also, the materials, sizes and proportions of the elements of the invention may be altered for various purposes and situations.

Figure 9:
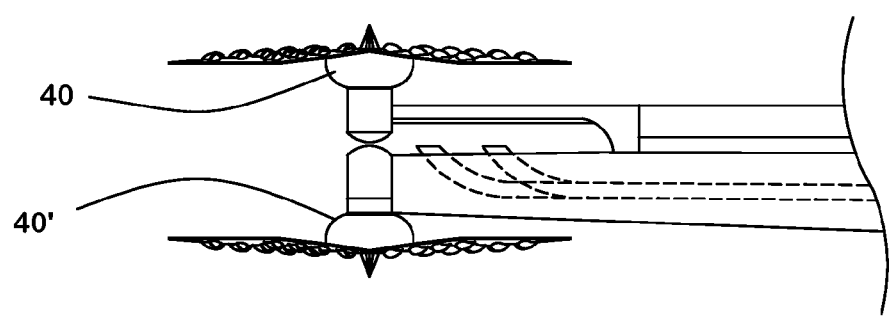
FIG. 9 shows an alternative form of the invention, having two opposed cutting heads.

As a further modification, a second rotary head may be positioned at the tip of the tool, the heads being substantially aligned on a common axis and facing in opposite directions so that opposite end plates may be prepared simultaneously. This modification is shown in FIG. 9, the second head being identified by reference 40'. The heads are independently driven, for example by respective drive shafts, or by independent motors at the tip of the probe 16 and the distal end of the lever 32. An advantage of providing independent drives is that the surgeon can vary the distance between the cutters while both are in operation. If the cutters are turned in opposite directions, reaction torques on the tool are canceled.

Considering the numerous modifications that are possible, the embodiment illustrated should be understood as only exemplary, and the invention should be measured by the claims below.

I claim:

1. A tool for preparing a surface of an end plate on a vertebral body, said tool comprising:
   a body,
   a rotary head supported on the body,
   a mechanism for turning the rotary head, and
   a cutting tool mounted on the rotary head, wherein
   the cutting tool is a flexible rasp which can deflect from its original shape to follow irregularities it encounters in the end plate without undergoing permanent deformation and
   the aspect ratio of the rasp is at least 3:1, so that it may be inserted through a small surgical aperture.

2. The invention of claim 1, further comprising at least one water supply line extending through the body to a port directed at the rotary head, to flush cuttings away, and at least one suction line extending through the body to at least one port.

\* \* \* \* \*